United States Patent [19]

Ross et al.

[11] 4,290,960

[45] Sep. 22, 1981

[54] PREPARATION OF 2,5-DIMETHYL-4-HYDROXY-2,3-DIHYDROFURAN-3-ONE

[75] Inventors: Karl-Heinz Ross, Mutterstadt; Christian Dudeck, Limburgerhof; Walter Himmele, Walldorf; Rolf Lebkuecher, Ludwigshafen; Wolfgang Sauer, Mannheim, all of Fed. Rep. of Germany

[73] Assignee: BASF Aktiengesellschaft, Ludwigshafen, Fed. Rep. of Germany

[21] Appl. No.: 127,467

[22] Filed: Mar. 5, 1980

[30] Foreign Application Priority Data

Mar. 15, 1979 [DE] Fed. Rep. of Germany ....... 2910131

[51] Int. Cl.$^3$ ................. C07D 303/14; C07D 307/32; C07D 307/20
[52] U.S. Cl. ......................... 260/348.57; 260/348.31; 260/347.8
[58] Field of Search ...................... 260/348.57, 348.31

[56] References Cited

U.S. PATENT DOCUMENTS

| | | | |
|---|---|---|---|
| 3,122,569 | 2/1964 | Kaman | 260/348.31 |
| 3,629,292 | 12/1971 | Evers | 260/347.8 |
| 3,887,589 | 6/1975 | Eykelboom et al. | 260/347.8 |
| 4,181,666 | 1/1980 | Huber et al. | 260/347.8 |
| 4,208,338 | 6/1980 | Huber et al. | 260/347.8 |

FOREIGN PATENT DOCUMENTS

8358 3/1980 European Pat. Off.

1212089 11/1970 United Kingdom.
1212090 11/1970 United Kingdom.
1440270 6/1976 United Kingdom.

OTHER PUBLICATIONS

Buchi et al., J. Org. Chem., vol. 38 (1973), pp. 123–125.
Buchi et al., J. Org. Chem., vol. 43 (1978) pp. 4765–4769.
Sheehan et al., J. Amer. Chem. Soc., vol. 74 (1952) pp. 3825–3828.

*Primary Examiner*—Norma S. Milestone
*Attorney, Agent, or Firm*—Oblon, Fisher, Spivak, McClelland & Maier

[57] ABSTRACT

A process for the preparation of the sought-after scent 2,5-dimethyl-4-hydroxy-2,3-dihydrofuran-3-one, and novel intermediates for the preparation of this compound.

2,5-Dimethyl-4-hydroxy-2,3-dihydrofuran-3-one is prepared by first epoxidizing hex-3-ene-2,5-diol in the liquid phase with hydrogen peroxide to give the novel compound 3,4-epoxy-hexane-2,5-diol, which at 40°–280° C. is converted, by means of a catalytic amount of an acid, to the novel compound 2,5-dimethyl-3,4-dihydroxy-tetrahydro-furan. The latter is dehydrogenated by means of oxygen over a silver catalyst or copper catalyst to give the nove compound 2,5-dimethyl-4-hydroxy-tetrahydrofuran-3-one, which is oxidized by means of bismuth oxide, in concentrated acetic acid solution, to give the desired compound 2,5-dimethyl-4-hydroxy-2,3-dihydrofuran-3-one.

1 Claim, No Drawings

PREPARATION OF 2,5-DIMETHYL-4-HYDROXY-2,3-DIHYDROFURAN-3-ONE

The present invention relates to a novel process for the preparation of 2,5-dimethyl-4-hydroxy-2,3-dihydrofuran-3-one (I)

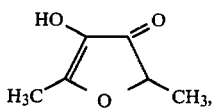

and to the novel intermediates in the preparation of this compound, namely 3,4-epoxy-hexane-2,5-diol (II), 2,5-dimethyl-3,4-dihydroxy-tetrahydrofuran (III) and 2,5-dimethyl-4-hydroxy-tetrahydrofuran-3-one (IV).

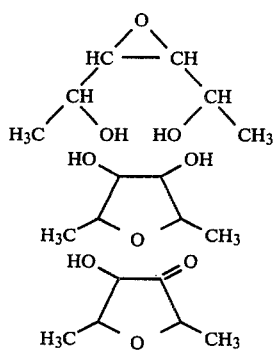

A plurality of processes for the synthesis of the natural fruit aromatic (I), which occurs in pineapples and strawberries, have been disclosed, but for various reasons these processes are unsatisfactory and cannot be economically transferred to industrial-scale operation.

For example, according to Büchi and Demole (J. Org. Chem, 38 (1973), 123f), 2,5-dimethyl-furanone is used as the starting material and converted, by treatment with bromine in methanol solution, to 2,5-dimethyl-2,5-dimethoxy-2,5-dihydrofuran, the latter compound is oxidized, by means of potassium chlorate and catalytic amounts of osmium tetroxide, to 3,4-dihydroxy-hexane-2,5-dione, and this compound can be cyclized, in the presence of bases, to (I). This synthesis is involved and requires the use of potassium chlorate, which presents certain problems, and of osmium tetroxide, which is expensive and very toxic, so that the synthesis is unsuitable for industrial operation.

A variant of this process, described by the same authors (loc. cit.), is equally unsatisfactory; in this variant the 3,4-dihydroxy-hexane-2,5-dione is merely prepared in a different way, namely by hydrodimerization of methylglyoxal in the presence of zinc dust. This reaction, which consists of a plurality of component operations, is difficult to control in sizable batches, and furthermore gives yields of only about 20%.

The process of German Pat. No. 2,105,014, by which 2,5-dihalo-hexane-3,4-diones are cyclized to (I) by means of aqueous alkali, is also not entirely satisfactory, since it gives yields of only about 30%.

In a similar process (German Laid-Open Application DOS No. 1,768,649), 2,5-dihydroxy-hexane-3,4-dione is converted to IIa. Since, however, this diol-dione can in turn only be prepared by ozonization of 2,5-dihydroxy-hex-3-yne, which is a reaction which is dangerous and difficult to control on an industrial scale, the industrial operation of the process once again entails difficulties.

Instead of the diol-diones, their esters, eg. the diacetates, have also been employed for cyclization to (I) (cf. German Laid-Open Application DOS No. 1,915,788). However, the preparation of these esters entails a Grignard reaction and an oxidation with potassium permanganate, ie. process steps which are known to demand precise observation of quite specific reaction conditions, thereby making the synthesis on an industrial scale clumsy and expensive.

In a further process (German Laid-Open Application DOS No. 2,359,891), which entails condensation of a sodium derivative of an acetoacetic acid ester and α-bromopropionyl chloride, followed by decarboxylation and oxidation, the yields achieved are only about 15%, based on the bromopropionyl chloride.

It is an object of the present invention to provide novel methods and novel starting compounds by means of which the sought-after aromatic (I) can be prepared more economically and by a simpler process than hitherto.

We have found that this object is achieved and that 2,5-dimethyl-4-hydroxy-2,3-dihydrofuran-3-one (I) is obtained economically, in good yield and by means of process steps which do not present technical problems, if (a) hex-3-ene-2,5-diol (V) is epoxidized in a conventional manner in the liquid phase, by means of hydrogen peroxide in the presence of an oxide of a metal of subgroups IV to VIII or of a heteropolyacid of one of the acid-forming elements of group VI of the periodic table of the elements, at a pH of from 3 to 7, preferably from 4 to 6, to give 3,4-epoxy-hexane-2,5-diol (II), (b) the resulting novel 3,4-epoxy-hexane-2,5-diol is converted in a conventional manner, by means of catalytic amounts of an acid, by cleavage of the epoxide ring and subsequent cyclization, to the novel compound 2,5-dimethyl-3,4-dihydroxy-tetrahydrofuran (III), (c) the resulting 2,5-dimethyl-3,4-dihydroxy-tetrahydrofuran is dehydrogenated by means of oxygen or of an oxygen-containing gas over a silver or copper catalyst, at from 400° to 700° C., to give the novel compound 2,5-dimethyl-4-hydroxy-tetrahydrofuran-3-one (IV) and (d) the resulting 2,5-dimethyl-4-hydroxy-tetrahydrofuran-3-one is oxidized with bismuth oxide, in concentrated acetic acid solution, to give 2,5-dimethyl-4-hydroxy-2,3-dihydrofuran-3-one.

The synthesis according to the invention can be represented as follows:

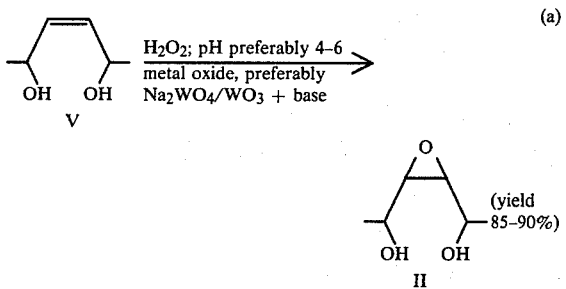

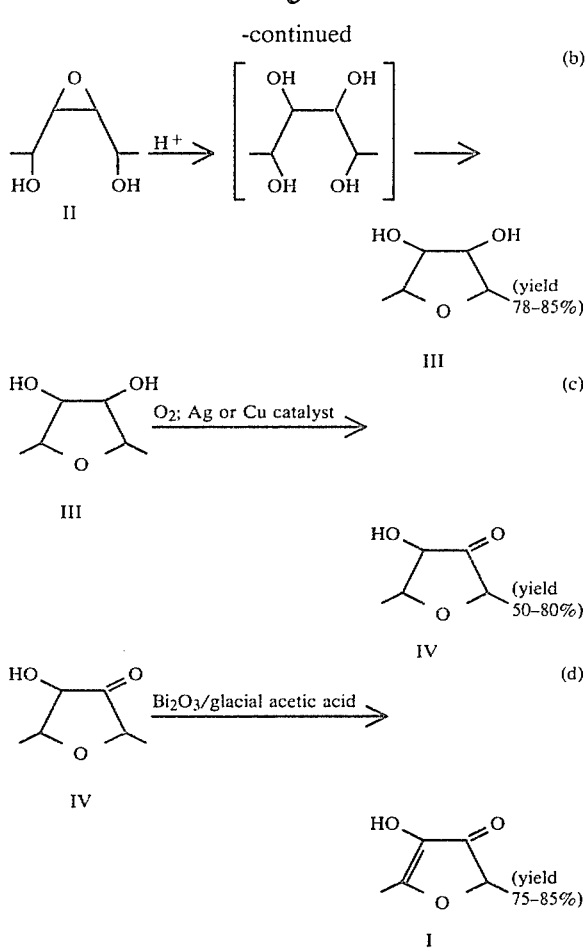

The overall yield over stages (a) to (d) is accordingly about 30 to 50%.

Hex-3-ene-2,5-diol, required for reaction step (a), is a known compound, which may, for example, be obtained in virtually quantitative yield by partial hydrogenation of the corresponding hexynediol by means of hydrogen over a palladium catalyst which has been partially deactivated, in accordance with German Patent 1,115,238, by means of zinc ions or lead ions.

Hex-3-yne-2,5-diol is a commercial compound which can be prepared by reacting acetylene with 2 moles of acetaldehyde.

Specifically, the component steps (a) to (d) of the process according to the invention may advantageously be carried out as follows:

(a) The preparation of 3,4-epoxy-hexane-2,5-diol is essentially carried out under the epoxidation reaction conditions disclosed in German Published Application DAS No. 1,144,276. Advantageously, a 20-50% strength by weight aqueous solution of hex-3-ene-2,5-diol (V) is used, and 1% by weight, based on V, of an oxide of a metal of sub-groups IV to VIII of the periodic table, eg. tungsten oxide, ruthenium tetroxide, vanadium tetroxide, molybdenum oxide or chromium trioxide, or of a heteropolyacid of one of the acid-forming elements of group VI of the periodic table, eg. a heteropoly-tungstic acid or molybdo-tungstic acid or chromo-tungstic acid, is suspended therein. Amongst the above metal oxides, tungsten oxide has proved particularly suitable. The suspension is then brought to a pH of 6-7 by means of a basic compound.

Suitable basic compounds are inorganic bases, eg. sodium hydroxide and sodium carbonate, but particularly organic amines, especially water-soluble amines, in general those of fewer than 15 carbon atoms, which may be aliphatic, cycloaliphatic, aromatic or heterocyclic, and include primary, secondary and tertiary amines. Examples of suitable aliphatic amines are methylamine, dimethylamine, ethylamine, diethylamine, di-n-propylamine, diisopropylamine, diisobutylamine, propylenediamine, diethylenetriamine, tetraethylenepentamine, propanolamine, ethanolamine and triethanolamine. Examples of suitable aromatic amines are aniline, methylaniline, dimethylaniline, toluidine, xylidine, diphenylamine and phenylenediamine. Suitable heterocyclic amines include pyridine, pyrrole, pyrrolidine, piperidine, morpholine, N-methylmorpholine, N-ethylmorpholine and lutidine.

Since the amines assist the epoxidation even at low concentration, it suffices to employ from 0.005 to 2% by weight of amine, based on the reaction mixture; an inorganic base may or may not be present at the same time. Hydrogen peroxide, advantageously in the form of a 30-50% strength by weight aqueous solution, is then added, in equimolar amount or in a slight excess over (V), gradually and whilst stirring, to the suspension obtained above, at 0°-100° C., preferably at 30°-60° C. The epoxidation, which in other respects can be carried out in accordance with German Published Application DAS No. 1,144,276, requires from about 3 to 12 hours. Working up the reaction mixture, which still contains metal oxides, by distillation gives II as a crude product in about 85-93% yield. The novel 3,4-epoxyhexane-2,5-diol is a viscous liquid which decomposes if its distillation is attempted.

(b) It is a particular advantage of the novel synthesis of (I) that the aqueous solutions obtained from process step (a) can be employed directly for the next stage (b), namely the preparation of 2,5-dimethyl-3,4-dihydroxytetrahydrofuran (III).

For this purpose, a catalytic amount of an acid is added to the solution and the mixture is heated at 40°-180° C., preferably 60°-120° C., for from about 0.5 to 3 hours. This first results in the formation of hexane-2,3,4,5-tetrol, which after having distilled off the water is dehydrated to III at from 0.2 to 50 mbar by raising the temperature further to a level required for distillation, namely 80°-280° C., preferably 120°-180° C.

Suitable acids are in particular mineral acids, eg. sulfuric acid, phosphoric acid and hydrochloric acid, strong organic acids, eg. formic acid and oxalic acid, and especially p-toluenesulfonic acid. Strong acid ion exchangers may also be used. For the purposes of the invention, the latter essentially include commercial cation exchangers based on polystyrenesulfonic acid resins or phenolsulfonic acid resins, and available, for example, under the following tradenames: Lewatit S 115, Amberlite JR 120, Dowex 50, Wolfatit KPS 200 and the like.

If it is preferred to start from pure II instead of from the reaction mixture obtained in process step (a), the pure II is advantageously diluted with a 2-fold to 5-fold amount of water, but in other respects the procedure described above is followed.

The novel compound 2,5-dimethyl-3,4-dihydroxytetrahydrofuran is a colorless viscous liquid which boils at 110° C./0.3 mbar and, according to analysis by gas chromatography, is a mixture of various stereoisomers.

(c) This dehydrogenation stage is a heterogeneous reaction over a copper, or preferably silver, fixed bed catalyst. The reaction takes place under the same conditions as the synthesis of formaldehyde from methanol, but it is unexpected that III does not undergo dehydration under the high temperatures of 480°-650° C., preferably 510°-580° C., which this reaction requires. The catalysts used are preferably agglomerates of silver crystals with particle diameters of from 0.01 to 2.5 mm. The use of particles of different sizes is preferred, since it results in a non-uniform bed, as a result of which the reaction takes place with higher selectivity. The thickness of the catalyst bed is preferably from 1 to 3 cm. Per hour, from 1 to 20 kg of III can be oxidatively dehydrogenated to IV over 1 kg of such a catalyst. Advantageously, the dehydrogenation is not carried out in a pure gaseous mixture of III and oxygen, but instead is carried out at high dilution.

It has proved advantageous to use air which has additionally been mixed with $N_2$, steam or acetone vapor. Suitable gaseous starting mixtures may have roughly the following composition: from 5 to 45% by volume of III, from 30 to 85% by volume of air, the remainder $N_2$ or $N_2$/water or $N_2$/acetone in the volume ratio of about 1:1.

After compound III and any other normally liquid constituents have been vaporized, the above components are passed as rapidly as possible downward through the catalyst bed which is at 480°-650° C. The yield of IV is the higher, the more rapidly the gas mixture, after passing through the catalyst, is chilled to a very low temperature, for example room temperature. This can be effected by washing the gases with cold water which is advantageously rendered slightly alkaline, ie. brought to a pH of 7–8, by means of sodium hydroxide solution, in order to stabilize compound IV. The residence time over the catalyst should be from about 0.001 to 0.1 second.

The water is stripped from the solution under reduced pressure (about 70-13 mbar) and the residue which hereupon remains is fractionated at from about 1.3 to 0.05 mbar. In addition to unconverted III (boiling point 105°-120° C./1 mbar), 2,5-dimethyl-4-hydroxy-tetrahydrofuran-3-one IV (boiling point 61°-66° C./1 mbar) is obtained in up to 85% yield, based on III converted. The conversion is from about 30 to 60%. If copper catalysts are used, the process details are the same but the conversion is somewhat lower.

The novel compound 2,5-dimethyl-4-hydroxy-tetrahydrofuran-3-one is an interesting fragrance and flavor material, which has a fruity odor and may be used in the preparation of cosmetic formulations, and for flavoring beverages and other foodstuffs. According to analysis by gas chromatography, the compound is a mixture of different stereoisomers.

(d) In process step (d), the oxidation of the ketol IV to (I) is carried out by Rigby's method (J. Chem. Soc. (1951), 793f) by first preparing a mixture of from 40 to 70% by weight of glacial acetic acid and from 25 to 50% by weight of bismuth oxide $Bi_2O_3$, then adding from 10 to 20% by weight of IV, and heating the mixture for from 10 to 30 minutes at 100°-130° C., preferably 110°-125° C., whereby a part of the $Bi_2O_3$ is reduced to metallic bismuth. After cooling the reaction mixture and filtering off the bismuth formed, the reaction mixture is worked up by distillation in a conventional manner. Advantageously, the distillation is carried out at from 0.05 to 0.5 mbar. Subsequent crystallization of the product from petroleum ether/chloroform in a conventional manner gives very pure furaneol.

EXAMPLE (a) Preparation of 3,4-epoxy-hexane-2,5-diol 414 g of 50% strength aqueous hydrogen peroxide (=1.1 mole per mole of hex-3-ene-2,5-diol) were added gradually in the course of 5 hours at 40°-50° C., whilst stirring, to a suspension of 696 g of 90% pure hex-3-ene-2,5-diol, 7.5 g of tungsten trioxide ($WO_3$), 5.5 g of N-methyl-morpholine and 2,400 g of water. The mixture was stirred for a further 17 hours at room temperature and then freed from water by distillation at 40° C. and 20 mbar. 722 g of a residue containing, according to epoxide determination, about 85% of 3,4-epoxy-hexane-diol were obtained. This corresponds to a yield of 86% of theory.

(b) Preparation of 2,5-dimethyl-3,4-dihydroxy-tetrahydrofuran

An aqueous solution obtained according to the first part of process step (a) was heated with 20 g of p-toluenesulfonic acid for 2 hours at 100° C. After removing the water by distillation under atmospheric pressure, the syrupy residue consisting of hexane-2,3,4,5-tetrol was heated at 95°-140° C./0.5 mbar, resulting in the formation of the furan, which distilled off under the stated conditions. 640 g of a distillate containing, according to analysis by gas chromatography, 88% of 2,5-dimethyl-3,4-dihydroxytetrahydrofuran were obtained. This corresponds to a yield of 79% of theory.

A purifying distillation gave 2,5-dimethyl-3,4-dihydroxy-tetrahydrofuran in 99% purity at 105°-112° C./0.3 mbar. According to analysis by gas chromatography (2 m of Carbowax, 100°-180° C.) and according to NMR spectroscopy, the product was a mixture of various stereoisomers.

(c) Preparation of 2,5-dimethyl-4-hydroxy-tetrahydrofuran-3-one (IV)

A vertical tubular reactor of 2 cm internal diameter, at the top of which 28 g of silver crystals (8 g of particles with diameters from 0.75 to 1 mm, 14 g of particles with diameters of from 0.4 to 0.75 mm and 6 g of particles with diameters of from 0.2 to 0.4 mm) were arranged, as a 2 cm thick bed, above a silver gauze screen, was fed, per hour, with a gaseous mixture, at 175° C., of 18.7 liters of 2,5-dimethyl-3,4-dihydroxy-tetrahydrofuran (=110 g), 72 liters of air and 100 liters of nitrogen. The catalyst temperature was 535° C. and the residence time over the catalyst about 0.04 second. After having passed over the catalyst, the gas mixture was immediately cooled to 20° C. by passing it into water. The resulting solution was brought to pH 8 with 10% strength NaOH solution. The water was then stripped off at 20 mbar and the residue was distilled at 1.3 mbar. This gave, at 61°-66° C., 35 g of a distillate containing about 80% of 2,5-dimethyl-4-hydroxy-tetrahydrofuran-3-one, and, at 109°-120° C., 60 g of unconverted 2,5-dimethyl-3,4-dihydroxy-tetrahydrofuran. The conversion was about 45% and the yield, based thereon, about 70%.

(d) Preparation of 2,5-dimethyl-4-hydroxy-2,3-dihydrofuran-3-one 17.5 g of 2,5-dimethyl-3,4-dihydroxy-tetrahydrofuran-3-one of about 80% purity were heated, in a suspension of 40 g of bismuth oxide and 50 g of glacial acetic acid, for 25 minutes at 120° C. After the reaction mixture had cooled, it was diluted with 80 g of ethyl acetate, whereupon metallic bismuth and bismuth acetate precipitated. The filtrate was fractionated, giving, at 85°–101° C./0.3 mbar, 14.2 g of a distillate containing about 77% of (I). This corresponds to a yield of 79%.

2.5 g of this fraction were taken up in a mixture of 2.8 g of chloroform and 1.6 g of petroleum ether, from which, after cooling, pure (I) of solidification point 75°–76° C. crystallized.

We claim:
1. 3,4-Epoxy-hexane-2,5-diol.

* * * * *